United States Patent [19]

Wahmi

[11] 4,374,824

[45] Feb. 22, 1983

[54] DENTIFRICE

[75] Inventor: Hakeem V. R. Wahmi, Hyderabad, India

[73] Assignee: Krishan Dyal Mathur, Alexandria, Va.

[21] Appl. No.: 228,791

[22] Filed: Jan. 27, 1981

[51] Int. Cl.$^3$ .......................... A61K 7/16; A61K 7/26
[52] U.S. Cl. ........................................ 424/58; 424/49
[58] Field of Search ................................... 424/49, 58

[56] References Cited

U.S. PATENT DOCUMENTS

| | | | |
|---|---|---|---|
| 115,719 | 6/1871 | Draper | 424/58 |
| 173,607 | 2/1876 | Fehr | 424/49 X |
| 1,386,252 | 8/1921 | Green | 424/58 X |
| 1,527,523 | 2/1925 | Nitardy et al. | 424/58 |
| 1,609,591 | 12/1926 | White | 424/58 |
| 1,968,858 | 8/1934 | Sheffield et al. | 424/49 |
| 2,024,146 | 12/1935 | Crowther | 424/58 X |
| 2,059,396 | 11/1936 | Ripert | 424/49 |
| 2,216,821 | 10/1940 | Long | 424/49 |
| 2,384,563 | 9/1945 | Roseman et al. | 424/49 |
| 2,658,851 | 11/1953 | Branderberger et al. | 424/49 |

FOREIGN PATENT DOCUMENTS

| | | | |
|---|---|---|---|
| 649902 | 9/1932 | Fed. Rep. of Germany | 424/58 |
| 613750 | 5/1935 | Fed. Rep. of Germany | 424/58 |
| 656808 | 2/1938 | Fed. Rep. of Germany | 424/58 |
| 1165813 | 10/1958 | France | 424/58 |
| 1439044 | 4/1966 | France | 424/58 |

OTHER PUBLICATIONS

Chem. Abstracts, vol. 1–94, entry "Almond", (1907–1981).
Hofer Massard Chem. Abstr. 22#3713(3), (1928) of Brit. 282088, Dec. 10, 1926.
Schwartz Chem. Abstr. 35#339(4), (1941) of Seifensieder Ztg. 67:416, (1940), "Almond Meal".
Guardiola Chem. Abstr. 47#10151a, (1953) of Ital. 467805, Dec. 22, 1951.
Miles Lab. Chem. Abstr. 66#5770r, (1967) of Brit. 1045041, Oct. 5, 1966.
Bonnet Chem. Abstr. 82#175141s, (1975) of Fr. Demande 2219774, Sep. 27, 1974.
Sachder Chem. Abstr. 82#1100n, (1975) of Indian 125090, May 4, 1974.
Baudot Chem. Abstr. 72#11516k, (1970) of Fr. 1,550,401, Dec. 20, 1968.
Pereira, "Elem. of Materia Medica and Therap.", pp. 233, 351–352, 496, 593–594, 764, 835, (Publ. 1854).
Merck Index, 9th Ed., 1976, entry 1899, 5583.
Griffith Universal Formulary (1854), Phila., Pa., pp. 100–102, 112–115, 175–177, 313, 351–352, 385, 431–432, 433–434, 452–453, 475–477.

*Primary Examiner*—Shep K. Rose
*Attorney, Agent, or Firm*—Sherman & Shalloway

[57] ABSTRACT

A dentifrice composition comprising 2.0–10.0% by weight ginger, 6.0–16.0% by weight magnesium silicate, 6.0–16.0% by weight sodium chloride; 6.0–16.9% by weight borax, 2.0–20.0% by weight catechu, 4.0–14.0% by weight piper nigrum, 4.0–14.0% by weight alum, 2.0–16.9% by weight seed and shell of sweet almond, 2.0–14.0% by weight pyrethrum, 4.0–20.0% by weight mastic, and 4.0–20.0% by weight tobacco, and the use thereof.

4 Claims, No Drawings

DENTIFRICE

BACKGROUND OF THE INVENTION

The present invention relates to a composition and method of dental treatment and more particularly to dentifrices and the preparation thereof.

Many different dentifrices for aiding the cleaning and preservation of the teeth have been marketed. These have been compounded uniformly on the theory that a clean tooth never decays. Accordingly, the only practical effect of these dentifrices for the most part has been to exercise a detergent, mildly scouring and antiseptic action on the teeth and surrounding tissues. In addition, it has been known to use in the dentifrice formulation therapeutic agents such as germicides, antibiotics, astringents or fluoride-containing compounds, typical examples of which include tyrothrycin, chlorophyllins, hexachlorophene, the sarcosides, astringent salts and water-soluble ionizable fluorine-containing compounds such as sodium fluoride, lithium fluoride, stannous fluoride, potassium fluoride, ammonium fluoride, sodium fluorostanite, stannous chlorofluoride, sodium monofluorphosphate, and the like.

It has been found that none of these prior art ingredients are effective in cleaning teeth, preventing caries and tooth diseases, and relieving some of the symptoms caused by tooth disease.

SUMMARY OF THE INVENTION

According to the present invention, there is prepared a dentifrice composition which is either in the form of a paste of a powder or a paste having as the active ingredients 2.0–10.0% by weight ginger, 6.0–16.0% by weight magnesium silicate, 6.0–16.0% by weight sodium chloride, 6.0–16.0% by weight borax, 2.0–20.0% by weight catechu, 4.0–14.0% by weight piper nigrum, 4.0–14.0% by weight alum, 2.0–16.0% by weight seed and shell of sweet almond, 2.0–14.9% by weight pyrethrum, 4.0–20.0% by weight mastic, and 4.0–20.0% by weight tobacco.

DETAILED DESCRIPTION OF THE INVENTION

The compilation of the ingredients into a dentifrice composition has been made because of the specific properties of each of the ingredients and that the combination has been found to complement each other in providing an effective dentifrice composition, which not only more effectively cleans the teeth, but assists in the prevention of caries, tooth disease and relieves the symptoms resulting from existing tooth and gum problems.

Ginger has been utilized in the present invention because it contains certain aromatic volatile oils which assist in relieving pain. In addition, dry ginger provides good cleaning ability with low abrasion. The ginger used is in the form of a powder and is the scraped, dried rhizome of *Zingiber officinalis* (Scitaminaceae).

Magnesium silicate is known for its use as an astringent and for use in the treatment of ulcers. Additionally, magnesium silicate provides a sufficient abrasive effect so as to assist in the prevention of the formation of tartar.

Sodium chloride has long been known for its use as a dentifrice. In addition, sodium chloride has long been used as an astringent in the treatment of wounds.

Borax is utilized for its effectiveness as an antiseptic, astringent and detergent. In addition, it provides a non-irritating wash for mucus membranes which makes it suitable for utilization during the presence of tooth disease.

Catechu is the extract of the dark heartwood of *Acacia catechu*. Because of the presence of catechin and other alkaloids, catechu is known to be effective as an astringent. However, in combination with the other ingredients of the dentifrice composition, it assists in the prevention of tooth disease.

Piper nigrum, from which black pepper is derived, contains volatile oils, piperine, piperdine, chavicin and other active ingredients and is recognized as containing carminative and mildly antipyretic properties. In addition, it has been found to enhance the cleaning of teeth and to assist in the prevention of tooth disease. In this invention, piper nigrum is in the form of a powder.

Alum has been utilized in prior dentifrice preparations and individually is known to have astringent and antiseptic properties.

Almond is used in the present composition not only to flavor the composition but, in addition, in assisting to relieve the symptoms associated with some tooth diseases. Blanched seed and shell of sweet almond, the seeds of variety dulcis of *prumus amygdalus communis* (Rosaceae) which are gound to a powder form are used in the present invention.

Pyrethrum which is the dried root of *anacyclus pyethrum* (Compositae) is a known dentalgia. However, in the present composition, its activity appears to be enhanced and it is especially advantageous in assisting to relieve the symptoms of a toothache. The pyrethrum is used in the form of a powder.

Mastic (Mastiche) which is the resinous exudation from *Pistacia lenticus* (Anacardiaceae) is utilized not only to enhance the flavor of the dentifrice composition but in addition to assist in the prevention of tooth decay. In the present invention, mastic is used in the form of a powder.

Tobacco has been found to be effective when utilized in the present composition to assist in relieving pain and attrition in swollen gums. For use in the present invention, the tobacco is the dried leaves of *Nicotiana Tobacum* and is in the form of a powder.

The dentifrice of this invention may also contain conventional well-known dentifrice ingredients such as humectants, detergents or surface-active agents, flavoring materials, sweetening agents, abrasives, coloring materials, anticaries agents, fungicidal or bactericidal agents, or water. The amount of these conventional dentifrice ingredients may be changed within the conventional ranges. Most commonly, in the case of a pasty dentifrice, the utilizable formula consists of 25–35% by weight water, 0.5–2.0% by weight of detergents or surface-active agents, 5–10% by weight humectants, 10–20% by weight of abrasives, and the remainder being the dentifrice ingredients of the present invention. Examples of the humectants include glycerol, sorbitol, maltitol, glucose, polypropylene glycol, polyethylene glycol and sodium pyrrolidone carboxylate.

Examples of other abrasives which may be utilized in the present invention are dicalcium phosphate dihydrate, calcium pyrophosphate, anhydrous dicalcium phosphate, insoluble sodium metaphosphate, hydrated alumina, calcium carbonate, magnesium carbonate, magnesium oxide, powdered silica, and the like.

Examples of the detergents or surface-active agents are sodium lauryl sulfate, sodium N-lauroyl silica sulfate, alphaolefin sulfonate, sodium lauryl ether sulfate, polyoxyethylene fatty acid esters, and the like.

Additional flavoring agents may also be incorporated into the composition such as peppermint oil, spearmint oil, sassafras oil, clove oil, sage oil, eucalyptus oil, marjoram oil, lemon oil, cinnamon oil, orange oil and sodium methylsalycylate.

Examples of the coloring agents, anticaries agents and fungicidal or bactericidal agents which may be utilized include sodium fluoride, stannous fluoride, hexachlorophene, and sodium fluorophosphate.

The manner of compounding the dentifrice in powder form to embody the ingredients of the present invention may be performed by any conventional operation whereby the ingredients are dried, ground to the desired particle size and then thoroughly mixed.

The dentifrice composition of the present invention may be in the form of a tooth powder or may be in the form of a toothpaste. The powder form is preferable; however, for illustrative purposes the following ingredients provide one method of compounding a suitable formulation:

Ginger: 113.3 grams (6.5% by weight)
Magnesium Silicate: 141.8 grams (9.6% by weight)
Sodium Chloride: 141.8 grams (9.6% by weight)
Borax: 141.8 grams (9.6% by weight)
Catechu: 141.8 grams (9.6% by weight)
Piper Nigrum: 141.8 grams (9.6% by weight)
Alum: 141.8 grams (9.6% by weight)
Blanched seed and shell of sweet almond: 141.8 grams (9.6% by weight)
Pyrethrum: 113.3 grams (6.5% by weight)
Mastiche: 141.8 grams (9.6% by weight)
Tobacco: 141.8 grams (9.6% by weight)

The manner of compounding the dentifrice in powder form is to thoroughly dry all of the materials, grind the materials to the desired particle size, and then sift through a very fine sieve, about number 60, before mixing. These dry materials are then thoroughly mixed.

To prepare a pasty dentifrice, the mixture is further admixed with about 25–35% by weight water and about 15% by weight humectants, e.g., glycerol.

Additionally, if desired, other materials may be incorporated into the dentifrice during the mixing stage so as to provide the dentifrice with any further characteristic desired.

The present invention is further illustrated in the following non-limiting examples.

EXAMPLE 1

Ginger root, tobacco leaves and the seed and shell of sweet almond are dried separately and stored in separate containers. To dry, one of the above materials is placed in an evaporating dish and heated slightly with a Bunsen burner until the material gets dry. The following amounts of the ingredients are used to prepare the present dentifrice:

Ginger: 3⅓ oz.
Silica of magnesia: 5 oz.
Rock salt: 5 oz.
Borax: 5 oz.
Catechu: 5 oz.
Piper Nigrum: 5 oz.
Alum: 5 oz.
Seed and shell of sweet almond: 5 oz.
Pyrethrum: 3⅓ oz.
Mastiche: 5 oz.
Tobacco: 5 oz.

Each of the above ingredients is ground in a mortar with a pestle until it is reduced to powder form. Thereafter, all of the ingredients are placed in a large mixer and mixed thoroughly. Coarse particles are separated from the mixture by sieving. The mixture of fine particles so obtained is dried by placing the same over mild heat for a minute, caution being taken not to overheat. The dried mixture is now ready for use as a dentifrice.

EXAMPLE 2

50 parts by weight of the dried powder obtained in Example 1, 35 parts by weight water and 15 parts by weight glycerol are mixed to form the dentifrice of the present invention which is in the form of a paste.

EXAMPLE 3

A male patient, age 20 was diagnosed to suffer from swollen and bleeding gums, bacterial infection, and plaque build-up on inner sufaces of teeth. The patient was given a tooth powder consisting of one ounce each of Rock Salt, Borax, Alum, and Piper Nigrum. The patient was to apply the tooth powder two to three times a day.

Three weeks after the patient's first visit, the gum conditions were found to have improved slightly. However, crystal deposit and plaque build-up were still present. The patient was instructed to use the same tooth powder for two months regularly for twice a day.

Three months after the above-mentioned examination, the patient was again examined and no significant change was found. As a result, one ounce each of Ginger and Catechu were added to the tooth powder previously prescribed to the patient. The patient was instructed to use the tooth powder regularly for two months.

After three months, the patient was examined. It was found that the bacteria infection and the bleeding had decreased slightly. However, the tooth powder was still not effective. Accordingly, the seed and shell of sweet almond and cinnamon were added to the tooth powder previously prescribed to the patient. The patient was instructed to use the tooth powder regularly for six months.

After seven months, the patient returned for an examination in which it was found that the condition of the teeth had improved, although crystal deposit and plaque formation still existed. A new dentifrice was prescribed to the patient, the dentifrice comprising the formulation of Example 1. The patient was instructed to use the dentifrice for six months and report for an examination at that time.

The patient was examined nine months after being given the new dentifrice. The condition of the teeth was found to have greatly improved. The pH of the saliva was lowered and the gums were not swollen. Crystal deposit and bacterial plaque formations were absent. The patient was given additional dentifrice and instructed to report only if teeth and gum conditions became unsatisfactory.

The patient was examined five years later. The teeth were found to be cleaner with very little plaque build-up. Tooth decay had practically stopped.

The patient was examined again five years later. The teeth were found to be in excellent condition.

EXAMPLE 4

A 48 year old male patient was examined and found to suffer from purulent inflammation, bleeding and swollen gums, gingivitis and heavy tartar build-up. A tooth powder consisting of the formulation of Example 1 was prescribed to the patient. The patient was instructed to use the tooth powder regularly two to three times a day and to report for a subsequent examination in two weeks.

After two weeks, the patient was re-examined. The general condition of the teeth showed improvement, although the patient complained of irritation of gums and emetic action sometimes. A dentifrice comprising the proportions shown in Example 1 was prescribed to the patient who was instructed to use it regularly and to report in two months.

An examination after three months of use of the new dentifrice showed marked improvement in the condition of the teeth. Plaque build-up, tooth decay, infection of gums were all reduced.

EXAMPLE 5

A 40 year old female patient was diagnosed to suffer from swollen and bleeding gums, profuse tartar build-up, and putrifaction of gums and teeth. Dental caries were found in six teeth and the enamel was tinted. The dentifrice according to Example 1 was given to the patient who was informed to report for a follow up examination in one or two months.

The patient returned in one and one-half months at which time significant improvement was noted. The tartar build-up had slowed and no new cavities were found. Bleeding of the gums had also stopped. The patient was instructed to continuously use the new dentifrice regularly.

The patient returned after two years at which time it was found that the gums were swollen and spongy. Two teeth were found infected and had to be removed. Crystal deposits were also found on the teeth. The patient indicated that she had discontinued use of the dentifrice soon after her condition had improved. The patient was instructed to use the dentifrice of Example 1 regularly and report for check-ups from time to time.

The patient returned regularly for check-ups for ten years. The condition of the teeth remained normal.

EXAMPLE 6

A 12 year old male patient was examined and found to suffer from swollen and bleeding gums, marginal gingivitis, inflammation of sockets of teeth and two cavities. A mixture of 1 oz. each of Rock Salt, Borax, Catechu, Piper Nigrum, and Alum was given to the patient to be used as a tooth powder for one month, two to three times every day.

Upon a return visit, the patient complained of occassional emetic condition. The gums were still swollen and a new cavity had developed. To the above dentifrice mixture, Mastiche and Pyrethrum were added. The patient was informed to report in a month.

The patients returned in about one month at which time the gums were found to have improved. However, overall condition of the teeth was still unsatisfactory since there was continued plaque build-up and bacterial infection. The patient was given the dentifrice of Example 1 and instructed to report for re-examination in two weeks.

Re-examination of the patient in two weeks showed remarkable improvements in the condition of the teeth. No cavities were formed. Plaque build-up had decreased. The patient was examined intermittently for fifteen years and no new cavities were found. The condition of the gums and teeth was found to be strong and healthy.

EXAMPLE 7

A 22 year old female patient was examined and found to suffer from swollen and bleeding gums, gingivitis, and three teeth with dental caries. A mixture comprising 1 oz. each of Rock Salt, Borax, Alum, Cinnamon and Piper Nigrum was given to the patient for application every day for two weeks.

Upon re-examination, no change in the condition of the teeth was noted. The formula was changed so that 1 oz. each of Ginger, Mastiche and Silica of magnesia were added to the dentifrice mixture. The patient was asked to apply the tooth powder regularly twice a day and to report for re-examination in two weeks.

A follow up examination showed that the gums were slightly improved. The patient was advised to continue using the same tooth powder for six months.

A follow up examination showed that dental caries developed in two more teeth. The patient was then given the dentifrice having the formula shown in Example 1. The patient was instructed to use the dentifrice for one month and report for a follow-up examination. One month afterward, an examination of the patient showed remarkable improvements in that no new dental caries were found. Less plaque build-up and infection of teeth were also found. The teeth were also found to be cleaner. The patient was provided with a new supply of the dentifrice for regular use and to report in six months. The patient returned in seven months and the conditions of the teeth were found to be excellent and no new cavities were found.

The patient was examined intermittently for the next twelve years. No abnormal plaque formations or crystal deposits were found. In addition, no new dental caries developed.

EXAMPLE 8

A 17 year old male patient was found to suffer from cough, swollen gums and having teeth infected with bacteria. A tooth paste comprising 1 oz. Borax, 2 ozs. Ginger, 2 ozs. Pepper, and 2 ozs. Salt mixed in honey and onion juice was given to the patient for application for two weeks.

The patient was re-examined after two weeks. Little impact on the condition of the teeth was found and that the gums were still swollen and the teeth were still infected. The tooth paste formulation was then changed to comprise 1.5 oz. Borax, 2 ozs. Ginger, 1 oz. Rock Salt, 1 oz. Pepper and 1.5 oz. Alum. The patient was instructed to apply the tooth powder two to three time a day.

The patient was examined after two weeks. It was found that the swelling in the gums had decreased but the patient developed two new cavities. Various formulations of tooth powder were given to the patient for a period of four years without any significant improvement. The patient was then given the dentifrice having the formulation shown in Example 1. The patient was instructed to use the dentifrice for two months and report for an examination.

The patient returned after two months for re-examination at which time it was found that the condition of the teeth had improved remarkably. There were no swollen gums, very little crystal build-up and plaque broke up from interproximal spaces. In addition, tooth decay had decreased. The patient was provided with the new dentifrice and instructed to use same regularly. The patient was examined intermittently for a period of ten years. No serious dental infection was observed and gum deterioration had practically stopped.

EXAMPLE 9

Upon examination, a 10 year old male patient was found to suffer from spongy gums, discolored teeth, crystal deposits and bacterial infection. The patient was given the dentifrice of Example 1 to be applied twice daily.

One month later, the condition of the gums and teeth were found to have improved considerably. The patient was examined intermittently for a period of twelve years. The patient maintained excellent teeth and no cavities were formed.

EXAMPLE 10

A 51 year old male patient was examined and found to have teeth of very dark color, six cavities, purulent inflammation of the sockets of the teeth and swollen gums. The teeth were cleaned and the dentifrice of Example 1 was given. The patient was asked to use the dentifrice twice a day. After three weeks, the condition of the teeth was found to be much better and no new cavities were formed. The patient was asked to use the dentifrice regularly and to report in two months.

After two months, the condition of the teeth had improved greatly. There was litte plaque formation and the bacterial infection was lessened. The patient was examined one year later and there was no formation of new cavities. The condition of the teeth was good and there was no plaque build-up.

The patient used the dentifrice regularly. An examination of the patient four years later showed no new cavities and the teeth were in good shape.

EXAMPLE 11

A 30 year old female patient was examined and found to have bacterial infection of teeth and bacterial plaque build-up on the surface of the teeth, gingivitis and dental caries in four teeth. The patient's teeth were also found to be dark colored. The patient was given the dentifrice of Example 1 with instructions to use the dentifrice regularly two to three times a day.

In a follow up visit two weeks later, the condition of the teeth were found to have improved remarkably. There was less plaque formation and less crystal deposits. The patient was asked to use the dentifrice regularly and to report for an examination in three months.

Upon re-examination, further improvements in the teeth was noted. The dark coloring of the teeth started to disappear. There were less infection, less plaque build-up and less tooth decay. The patient was advised to use the dentifrice regularly. One year later, the patient was examined at which time it was found that the teeth were cleaner, no new cavities were formed and there was very little crystal deposits. The patient was advised to brush her teeth with the dentifrice regularly.

Five years later, the patient was examined and no signs of teeth decay were found.

EXAMPLE 12

Upon examination, a 35 year old male patient was found to have a sore throat and ulcerated gums. The patient also complained of toothache. The patient's teeth were cleaned. The patient was given a tooth powder comprising Ginger, Rock Salt, Piper Nigrum and Cinnamon.

After three weeks, the patient returned for a follow up examination at which time the sore throat was gone. The patient was given more tooth powder and asked to return in a month. However, the patient did not return until three years later at which time the condition of the teeth had worsened. The patient complained that the tooth powder previously provided had not been effective. Examination of the patient showed that he was suffering from gingivitis, loose teeth and discharge of pus and bleeding from gums. The patient was given the dentifrice of Example 1 and advised to use the dentifrice regularly.

After one month, the condition of the teeth was much improved. There were no new dental caries and less plaque build-up. The patient was instructed to use the tooth powder regularly.

After two months, the patient reported for a follow up examination in which no bleeding of gums was found. Plaque build-up was also lessened. The patient was instructed to continue the regular application of the dentifrice and report for an examination in two months.

After two months, the condition of the teeth had greatly improved. There were no loose teeth and no new dental cavities. The patient was advised to use the tooth powder regularly.

Five years later, the patient was examined and the teeth were found to be in excellent condition.

Ten years later, the patient was examined and the teeth were found in excellent condition. The patient had used the dentifrice regularly.

The above Examples show that in the present invention, a unique combination of specific ingredients in the proper proportions brings forth unusually excellent results. The present dentifrice inhibits crystal deposits and dark coloration of teeth which could harm enamel; effectively controls plaque formation by constantly breaking tartar crystals and other matter even from the interproximate spaces of the teeth and gingival margins; and prevents dental caries and other tooth diseases. By using the present dentifrice, there is very little gum deterioration due to bacterial infection and other causes. The regular use of the present dentifrice cures teeth problems of people of all ages, male or female. As long as the patient brushes with the present dentifrice, gums are constantly strengthened, tooth decay is greatly reduced and the teeth remain healthy for a prolonged period of time.

What is claimed is:

1. A dentifrice composition comprising 2.0–10.0% by weight ginger, 6.0–16.0% by weight magnesium silicate, 6.0–16.0% by weight sodium chloride, 6.0–16.0% by weight borax, 2.0–20.0% by weight catechu; 4.0–14.0% by weight piper nigrum, 4.0–14.0% by weight alum, 2.0–16.0% by weight seed and shell of sweet almond, 2.0–14.0% by weight pyrethrum, 4.0–20.0% by weight mastic, and 4.0–20.0% by weight tobacco.

2. The dentifrice composition of claim 1 comprising 6.5% by weight ginger, 9.6% by weight magnesium silicate, 9.6% by weight sodium chloride, 9.6% by weight borax, 9.6% weight catechu, 9.6% by weight piper nigrum, 9.6% by weight alum, 9.6% by weight seed and shell of sweet almond, 6.5% by weight pyrethrum, 9.6% by weight mastic, and 9.6% by weight tobacco.

3. The dentifrice composition of claim 1 including 25-35% by weight water and 5-10% by weight humectants.

4. A method for cleaning teeth and preventing tooth disease comprising applying the composition of claim 1 to the teeth and gums.

* * * * *